(12) United States Patent
Luther et al.

(10) Patent No.: US 6,238,693 B1
(45) Date of Patent: May 29, 2001

(54) TRANSDERMAL ADMINISTRATION OF FENOLDOPAM

(75) Inventors: Robert R. Luther, Reno, NV (US); Dawn McGuire, Berkeley, CA (US); Vandana Mathur, San Francisco, CA (US); David J. Ellis, Los Altos, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/300,092

(22) Filed: Apr. 27, 1999

Related U.S. Application Data (60) Provisional application No. 60/083,145, filed on Apr. 27, 1998.

(51) Int. Cl.[7] .................................................. A61F 13/02
(52) U.S. Cl. .................. 424/448; 604/890.1; 604/892.1; 604/30; 604/31; 60/2; 60/44
(58) Field of Search .................. 424/448; 604/890.1, 604/892.1, 30, 31; 607/2, 44

(56) References Cited

U.S. PATENT DOCUMENTS 4,197,297   4/1980   Weinstock .
4,861,771   8/1989   Gaitanopoulos et al. .

FOREIGN PATENT DOCUMENTS

WO 91/16041   10/1991   (WO) .

OTHER PUBLICATIONS

Brogden, R. N. and Markham, A., "Fenoldopam A Review of its Pharmacodynamic and Pharmacokinetic Properties and Intravenous Clinical Potential in the Management of Hypertensive Urgencies and Emergencies" *Drugs* (1997) 54(4):634–650.

Lokhandwala, M. F., "Preclinical and Clinical Studies on the Cardiovascular and Renal Effects of Fenoldopam: A DA–1 Receptor Agonist" *Drug Development Research* (1987) 10:123–134.

*Primary Examiner*—Michael A. Williamson
(74) *Attorney, Agent, or Firm*—Judy M. Mohr; Iota Pi Law Group (57) ABSTRACT

Transdermal administration of fenoldopam, both the racemic mixture and the active R-fenoldopam enantiomer, is described. Also described are transdermal patches for therapeutically effective transdermal administration of racemic fenoldopam and its active R-fenoldopam enantiomer to a subject in need of treatment for impaired renal function or hypertension.

9 Claims, 4 Drawing Sheets

TRANSDERMAL ADMINISTRATION OF FENOLDOPAM

This application claims the benefit of U.S. Provisional Application No. 60/083,145, filed Apr. 27, 1998, incorporated herein by reference in its entirety.

FIELD OF THE INVENTION

The present invention relates to transdermal administration of fenoldopam and to methods for administering the compound.

BACKGROUND OF THE INVENTION

Fenoldopam is a dopamine agonist that causes peripheral vasodilation via stimulation of dopamine type-1 receptors. The drug is currently administered as an intravenous infusion of racemic fenoldopam mesylate (CORLOPAM®) and is typically used in clinical situations where, either due to underlying disease or induced by trauma or a medical procedure, an elevation in blood pressure occurs requiring immediate correction. In these situations, fenoldopam can be given at a dose of between about 0.01–1.6 $\mu$g/kg/min for up to 48 hours to achieve a dose-dependent steady-state plasma concentration in about 20 minutes.

In addition to producing a decrease in blood pressure, fenoldopam also causes renal vasodilation, diuresis and natriuresis. Intravenous infusion of therapeutic dosages of fenoldopam increases renal blood flow and decreases renal vascular resistance while maintaining glomerular filtration rate and increasing creatinine clearance, urinary flow and excretion of sodium and potassium (Brogden, R. N. and Markham, A., *Drugs*, 54(4):634–650 (1997)). These beneficial effects of fenoldopam on renal function are particularly desirable for hypertensive patients with compromised renal function.

However, the antihypertensive and renal effects of fenoldopam are short lasting, due to the 3,4-dihydroxy benzene ring in the molecule and therefore a high first-pass metabolism via sulfation and glucuronidation (Lokhandwala, M. F., *Drug Development Research*, 10:123–134 (1987)). The average clearance (CL) and half-life ($t_{1/2}$) of racemic fenoldopam are 2.6 L/min and 4.6 min, respectively. Because of the high first-pass metabolism and short half-life, it is difficult to maintain a therapeutically effective concentration via oral administration and for a continuous therapeutic effect frequent dosing, i.e., intravenous infusion, is required. Intravenous administration has numerous drawbacks, including the need for a skilled professional, poor patient acceptance and the limitation on patient mobility.

There is, therefore, an interest in developing alternative modes of delivery for fenoldopam which provide a therapeutically effective blood concentration of the drug for a desired period of time, typically between 6–24 hours.

Transdermal administration of a drug is one approach to achieving a constant blood level of drug in a patient for a period of time. Transdermal administration is often considered as an alternative mode of delivery for some drugs, since in addition to the benefit of a more constant blood level, other benefits are realized, including more efficient utilization of the drug, the potential for localized, site specific delivery and less frequent administration (Baker, R. W., *CONTROLLED RELEASE OF BIOLOGICALLY ACTIVE AGENTS*, John Wiley and Sons, New York, (1987) p. 5–10). More efficient utilization of the drug is an important benefit, since oftentimes less drug, when administered in a controlled release manner, is required to produce a given duration of effect than when administered conventionally. This is particularly true if the half-life of the drug is short compared with the desired treatment period. Since the drug is utilized more efficiently, a considerably lower dose may be required, depending on the drug half-life and the desired time of treatment However, it is well known in the art of transdermal drug delivery that not all drugs can be successfully administered transdermally. Two of the common problems encountered with transdermal administration of an agent include (i) inability of the drug to penetrate the skin at a rate sufficient to achieve a therapeutic blood level and (ii) skin irritation.

Figure 1:
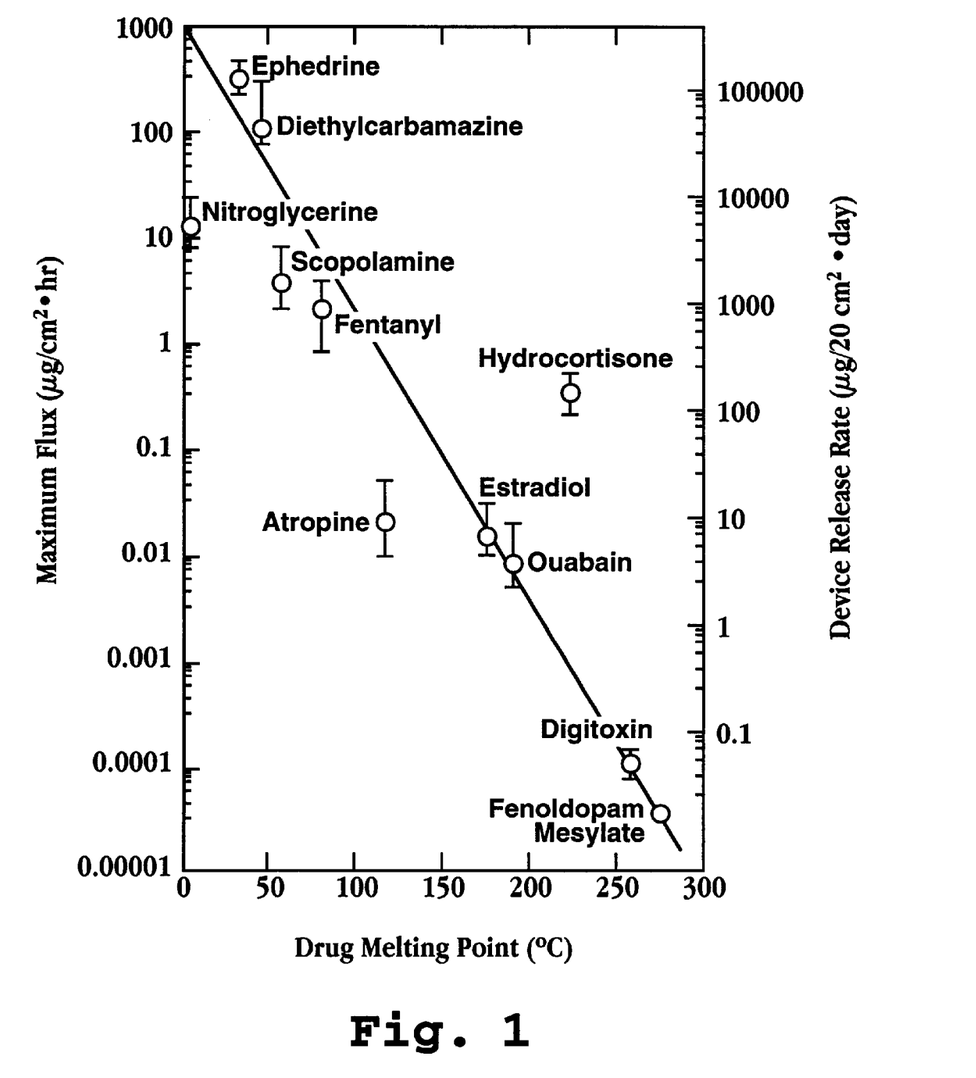
FIG. 1 shows the relationship between the skin flux rate of various drugs and the melting point of the drug.

One approach to predicting whether or not a selected drug will have a skin penetration rate sufficient for therapeutic efficacy is to correlate the melting point of the drug with the skin permeability (Baker, supra). The relationship between the skin flux rate of various drugs and their melting points is shown in FIG. 1 (from Baker, supra). Fenoldopam mesylate has a melting point of 274° C., which corresponds to a predicted skin flux rate of less than 0.0001 $\mu$g/cm$^2$·hr. The recommended daily dose of fenoldopam for hypertension is between 10–24 $\mu$g/day, which corresponds to a skin flux rate of 21–50 $\mu$/cm$^2$·hr from a 20 cm$^2$ patch. Thus, to achieve this dose at the predicted skin flux rate would require either an impracticably large patch size or a very significant improvement in skin flux rate by a skin permeation enhancer.

The free base form of fenoldopam may have a different melting point which, if lower, would favor an increase in the predicted skin flux rate. However, it is unknown if any lowering in the melting point would be sufficient to achieve a skin flux rate sufficient to achieve a therapeutically effective dose. Moreover, the free base is readily oxidized, necessitating that precautions be taken to protect the drug from exposure to the atmosphere during storage of a transdermal dosage form, e.g., a oxygen impermeable storage packet or addition of an anti-oxidant to the formulation.

Fenoldopam is a chiral compound and is currently administered as a racemic mixture of its optical isomers, called enantiomers. Enantiomers are structurally similar compounds having identical physical properties, except for the direction in which they rotate polarized light. Although enantiomers are physically similar, they can have profoundly different effects in biological systems, where one enantiomer is biologically active while the other has little or no biological activity. This is the case for the enantiomers of fenoldopam, where the activity of the drug is due to the R-enantiomer, the S-enantiomer being relatively inactive.

It is unknown if the skin flux rate of the enantiomers is sufficient to achieve a therapeutic blood level for treatment of the indications, discussed herein, fenoldopam is typically administered.

SUMMARY OF THE INVENTION

Accordingly, it is an object of this invention to transdermally administer fenoldopam at a rate which attains a therapeutic blood level for treatment of conditions ameloriated by the drug fenoldopam, including but not limited to impaired renal function and hypertension.

It is another object of this invention to transdermally administer the active enantiomer of fenoldopam at a rate which attains a therapeutic blood level for treatment of such conditions.

It is another object of the invention to provide a transdermal patch that can deliver racemic fenoldopam or the pharmacologically active enantiomer of fenoldopam at a rate that attains a therapeutic blood level for treatment of a selected condition.

Another object of the present invention is to provide a fenoldopam transdermal patch that is less than or equal to 30 cm² in active surface area.

It is a further object of the invention to provide a transdermal patch for administration of fenoldopam, either the racemic mixture or the active R-fenoldopam enantiomer, that avoids or minimizes skin irritation. Another object of the invention is to provide a fenoldopam transdermal patch that is effective for a period of at least about 12 hours.

In one aspect, the invention includes a method of administering fenoldopam to a patient, comprising transdermally administering to the patient an amount of fenoldopam sufficient to achieve a therapeutic plasma concentration.

In one embodiment, racemic fenoldopam is administered transdermally to the patient, and in another embodiment, the active R-fenoldopam enantiomer is administered transdermally.

In another embodiment, R-fenoldopam is administered transdermally along with an amount of S-fenoldopam which is effective to enhance the skin permeation rate of R-fenoldopam.

In one embodiment, the method includes applying to the skin of the patient a transdermal patch effective to achieve a fenoldopam skin permeation rate sufficient to obtain the desired therapeutic plasma concentration. In one embodiment, the fenoldopam skin permeation rate is between about 1–20 $\mu g/cm^2 \cdot hr$ and the patch includes an amount of fenoldopam sufficient to maintain such a rate for a period of at least about 12 hours.

The transdermal patch, in one embodiment, includes a penetration enhancer effective to enhance transdermal uptake of fenoldopam, and the patch is designed to release the enhancer in an effective amount over the drug-release period of the patch.

In another embodiment, the method includes (i) applying to the skin of the patient, an iontophoretic drug delivery device effective, with application of a selected iontophoretic current, to achieve a fenoldopam skin permeation rate sufficient to obtain the therapeutic plasma concentration, and (ii) applying such a current.

In one embodiment, fenoldopam is administered transdermally to achieve a plasma concentration effective for treatment of impaired renal function. In another embodiment, the drug is administered transdermally at a rate sufficient to achieve a therapeutic plasma concentration for treatment of hypertension.

In another aspect, the invention includes a transdermal delivery device for administering racemic fenoldopam or R-fenoldopam to a subject. The patch includes (i) an impermeable backing layer; (ii) a matrix or reservoir adjacent the backing layer, and containing racemic fenoldopam or R-fenoldopam distributed therein in an amount sufficient for release over at least a 6-hour period at a skin permeation rate sufficient to achieve a therapeutic blood concentration; and (iii) a removable impermeable layer to prevent drug release from the matrix or reservoir prior to use.

The device, in one embodiment, further includes a penetration enhancer in the matrix or reservoir, where the enhancer is effective to enhance transdermal uptake of racemic fenoldopam or R-fenoldopam.

In another embodiment, the matrix or reservoir includes R-fenoldopam and an amount of S-fenoldopam, at a ratio of R:S fenoldopam enantiomers, which is effective to enhance the skin permeation rate of R-fenoldopam.

In another embodiment, racemic fenoldopam or R-fenoldopam is entrapped in particles distributed throughout the reservoir or matrix of the transdermal device, and the particles are effective to release entrapped drug at a rate sufficient to achieve the desired skin permeation rate. Such particles, in one embodiment are composed of a hydrophilic polymer selected from the group consisting of polyvinyl alcohol, polyvinylpyrrilodone, polyacrylic acid and celluloses. In another embodiment, the particles are liposomes.

The transdermal device, in another embodiment, includes a contact surface adjacent the reservoir or matrix, the contact surface selected from a drug-permeable membrane and an adhesive.

These and other objects and features of the invention will be more fully appreciated when the following detailed description of the invention is read in conjunction with the accompanying drawings.

DETAILED DESCRIPTION OF THE INVENTION

I. Definitions

In describing and claiming the present invention, the term "fenoldopam" refers to the compound having the chemical name 6-chloro-2,3,4,5-tetrahydro-l-(4-hydroxyphenyl)-1H-3-benzazepine-7,8-diol with the following structure:

and is intended to include the racemic mixture, the R-enantiomer and the S-enantiomer and to mixtures of the R and S enantiomers in any proportion. The racemate and the enantiomers can be a free base or a salt, such as hydrochloride, mesylate, hydrobromide, tromethamine, or the like.

The term "R-fenoldopam" as used herein refers to the active enantiomer of fenoldopam free base and its pharmaceutically effective salts, the active enantiomer being substantially free of the inactive enantiomer, S-fenoldopam. Methods for resolution of the enantiomers and isolation of R-fenoldopam are known in the art, for example, as described in *Acta Pharmaceutica Suecica,* Suppl. 2, 1983, pages 132–150.

The term "racemic fenoldopam" or "racemate" as used herein refers to an equal mixture of the active and inactive enantiomers of fenoldopam, in base form or in a salt form.

As used herein, the term "enhancer" is meant to encompass any solvent or combination of solvents that increases the permeability of fenoldopam to the stratum corneum and/or the underlying dermal layers.

The term "therapeutic plasma concentration" or "therapeutic blood concentration" are used interchangeably and refer to a concentration of fenoldopam or its active enantiomer in the blood of a subject which is effective to treat or ameliorate a given indication. For example, a therapeutic concentration for treatment of impaired renal function or for treatment of hypertension are known and/or are readily determined to those of skill in the art using well-known scientific principles.

II. Transdermal Delivery of Fenoldopam

As discussed above, the physico-chemical characteristics of fenoldopam mesylate, the form of the drug commercially available for administration, make it difficult to deliver transdermally a therapeutically effective dose of the drug. The applicants have discovered, however, that fenoldopam in selected dosage forms can be administered transdermally at a blood level sufficient for therapy of impaired renal function, both chronic and acute renal failure, as discussed below. More particularly, the applicants have found that racemic fenoldopam and its active R-fenoldopam enantiomer can be delivered transdermally from transdermal delivery devices at a skin flux sufficient to achieve a blood concentration effective for treatment of impaired renal function.

In studies performed in support of the invention, the in vitro skin flux rate of fenoldopam mesylate and fenoldopam base through human skin w as measured from various solutions. Also in support of the invention, dermal sensitization studies of fenoldopam mesylate and the active R-enantiomer of fenoldopam mesylate were conducted. The results of these studies will now be discussed.

A. In vitro Skin Flux

Figure 2A:
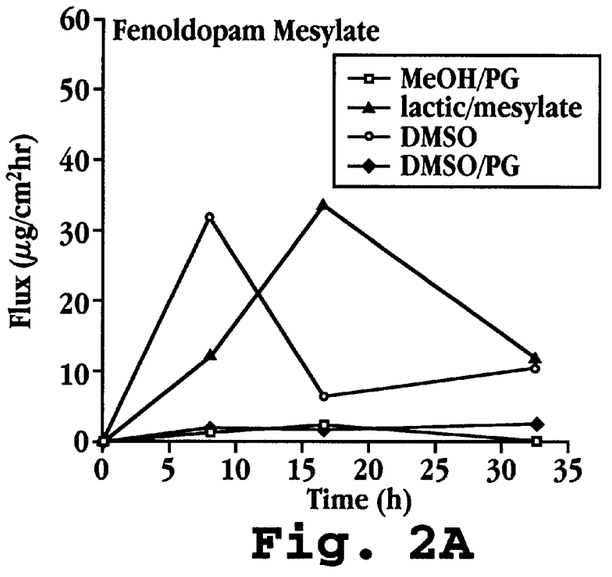
FIGS. 2A–2B show the in vitro flux rate, in $\mu g/cm^2 \cdot hour$, (FIG. 2A) and the cumulative flux, in $\mu g/cm^2$, (FIG. 2B), of fenoldopam mesylate through human cadaver skin, from saturated solutions of the drug in methanol/propylene glycol (open squares), lactic acid plus mesylate salt (closed triangles), dimethylsulfoxide (DMSO, open circles) and a mixture of DMSO/propylene glycol (closed diamonds)

The skin flux rate of fenoldopam mesylate and the free base were measured in vitro, according to the procedure described in Example 1, using human cadaver skin. Skin permeation of the mesylate salt form of the drug was determined from saturated solutions of the drug in a mixture of methanol/propylene glycol (90/10), a mixture of lactic acid and mesylate salt, dimethylsulfoxide (DMSO) and a mixture of DMSO/propylene glycol (1:2 vol/vol). The skin flux for the fenoldopam mesylate is shown in FIG. 2A and the cumulative release is shown in FIG. 2B.

As discussed above in the Background section, the minimum recommended dose of fenoldopam mesylate for treatment of hypertension is 10 mg/day, with a recommended dose of 24 mg/day. To achieve these dosages, a skin flux rate from a 20 $cm^2$ patch of between 21–50 $\mu g/cm^2 \cdot hr$ would be required. The results in FIG. 2A show this skin flux rate is attainable, in particular the fenoldopam mesylate formulations of DMSO (open circles) and lactic acid/mesylate salt (closed triangles), achieved skin flux rates of greater than 30 $\mu g/cm^2 \cdot hr$, prior to depletion of the drug from the donor compartment. The formulations using DMSO/propylene glycol (closed diamonds) and methanol/propylene glycol (open squares) are also shown in the figure.

Figure 2B:
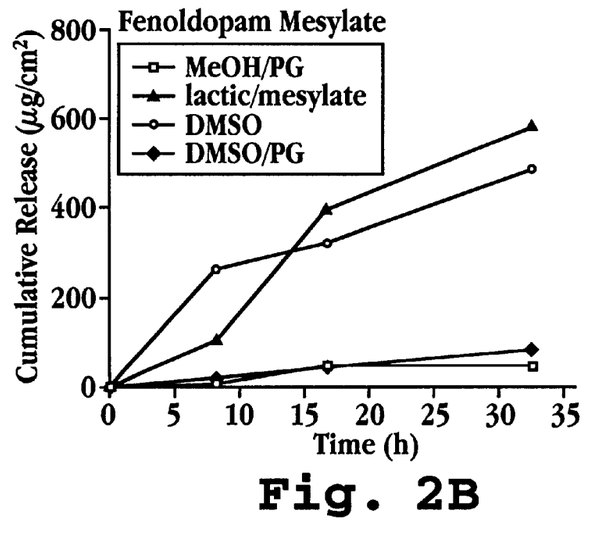

As seen in FIG. 2B, about 400 $\mu g/cm^2$ of fenoldopam mesylate had permeated the skin from the formulation of DMSO.

Thus, a transdermal patch of 25 $cm^2$ in size would achieve the 10 mg/day minimum dosage for treatment of hypertension. The lactic acid/mesylate salt formulation had a higher release, with nearly 500 $\mu g/cm^2$ of fenoldopam mesylate permeated after 24 hours. Thus, a patch of 20 $cm^2$ in size would achieve the 10 mg/day minimum dosage and a 48 $cm^2$ patch would achieve the 24 mg/day dosage.

Figure 3A:
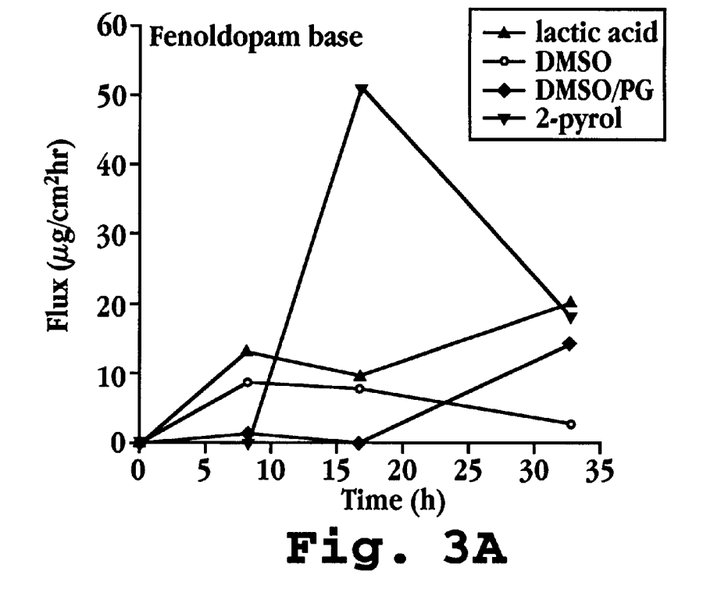
FIGS. 3A–3B show the in vitro flux rate, in $\mu g/cm^2 \cdot hour$, (FIG. 3A) and the cumulative flux, in $\mu g/cm^2$, (FIG. 3B), of fenoldopam base through human cadaver skin, from saturated solutions of the drug in lactic acid (closed triangles), dimethylsulfoxide (DMSO, open circles); a mixture of DMSO/propylene glycol (closed diamonds) and 2-pyrrolidone (inverted triangles)
Figure 3B:
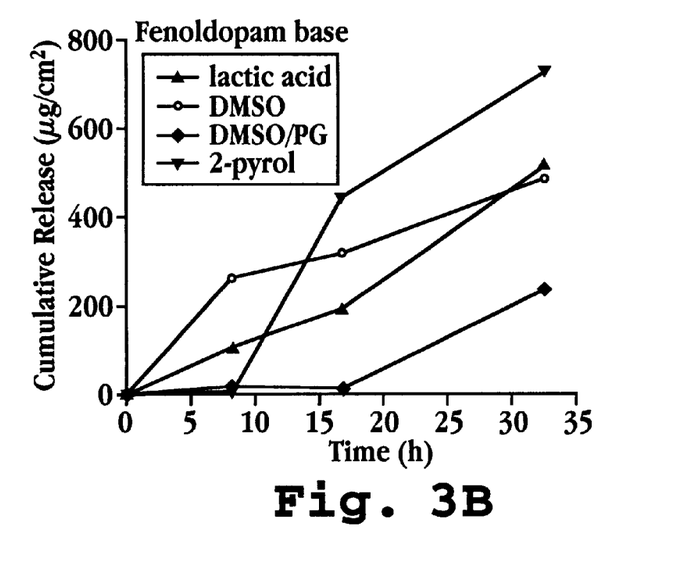

FIGS. 3A–3B show the results of the skin permeation studies using fenoldopam free base from saturated solutions of the drug in lactic acid (closed triangles), dimethylsulfoxide (DMSO, open circles); a 1:2 vol/vol mixture of DMSO/propylene glycol (closed diamonds) and 2-pyrrolidone (inverted triangles). As seen in FIG. 3B, the cumulative release of the base from the solutions of 2-pyrrolidone and lactic acid is sufficient to administer a therapeutically effective dose of fenoldopam from a transdermal patch of less than 20 $cm^2$ in size.

B. In vivo Dermal Sensitization Studies

Dermal sensitization studies in guinea pigs were done to assess the contact sensitization of fenoldopam mesylate and of R-fenoldopam mesylate, the active enantiomer, when administered topically and intradermally. Each of the drugs, the fenoldopam mesylate and the R-fenoldopam mesylate, were administered to the animals from a 50:50 mixture of propylene glycol/water, at drug concentrations of 40 mg/mL, 30 mg/mL, 20 mg/mL, and 10 mg/mL.

As described in Example 2, sixteen animals were divided into 4 groups of 4 animals each. The first group of 4 animals (Group 1) were treated with a topical application of fenoldopam mesylate at the four concentrations. Each animal, after having the hair removed from its back and sides, received each of the concentrations applied at four separate sites. The animals in Group 2 were similarly treated, except with R-fenoldopam. After 24 hours of exposure to the test material, the application site was scored on a four-point scale for dermal reactions (0=no reaction, 1=moderate mild redness, 2=moderate and diffuse redness, 3=intense redness and swelling). The results are shown in Table 2.

TABLE 2

Individual Body Weights and Dermal Reactions -
Irritation Screening Study
Topical Application

| | | Dermal Reactions Test Material Concentration (mg/ml in PG/SW*) | | | | | | | |
|---|---|---|---|---|---|---|---|---|---|
| | Body | 10 mg/mL Hour | | 20 ml/mL Hour | | 30 mg/mL Hour | | 40 mg/mL Hour | |
| Animal Number | Weight (g) | 24 | 48 | 24 | 48 | 24 | 48 | 24 | 48 |
| Fenoldopam Mesylate | | | | | | | | | |
| 1 | 494 | 0 | 0 | 0 | 0 | 0 | 0 | 0 | 0 |
| 2 | 484 | 0 | 0 | 0 | 0 | 0 | 0 | 0 | 0 |
| 3 | 501 | 0 | 0 | 0 | 0 | 0 | 0 | 0 | 0 |
| 4 | 487 | 0 | 0 | 0 | 0 | 0 | 0 | 0 | 0 |
| R-Fenoldopam Mesylate | | | | | | | | | |
| 5 | 495 | 0 | 0 | 0 | 0 | 0 | 0 | 0 | 0 |
| 6 | 503 | 0 | 0 | 0 | 0 | 0 | 0 | 0 | 0 |
| 7 | 519 | 0 | 0 | 0 | 0 | 0 | 0 | 0 | 0 |
| 8 | 439 | 0 | 0 | 0 | 0 | 0 | 0 | 0 | 0 |

*Test material in 50% propylene glycol/50% sterile water mixture.

The results from the topical application indicate that the drug in both forms, e.g., as the mesylate salts of the racemic mixture and the active R-enantionmer, can be administered as 40 mg/mL mixtures in 50% propylene glycol/50% sterile water with no dermal reaction.

Dermal sensitization was also evaluated following intradermal injection of fenoldopam mesylate and R-fenoldopam at the same concentrations used in the topical screening. As described in Example 2, four animals (Group 3) were treated with 1 mL injections of fenoldopam mesylate at four injection sites, one for each of the four concentrations. Four animals in Group 4 were similarly injected with R-fenoldopam at the four concentrations. 24 hours after injection, the injection sites were scored for dermal reaction on the 4-point scale. The results are shown in Table 3.

TABLE 3

Individual Body Weights and Dermal Reactions -
Irritation Screening Study
Intradermal Injection

| | | Dermal Reactions Test Material Concentration (mg/mL in PG/SW*) | | | | | | | |
|---|---|---|---|---|---|---|---|---|---|
| | Body | 10 mg/mL Hour | | 20 ml/mL Hour | | 30 mg/mL Hour | | 40 mg/mL Hour | |
| Animal Number | Weight (g) | 24 | 48 | 24 | 48 | 24 | 48 | 24 | 48 |
| Fenoldopam Mesylate | | | | | | | | | |
| 9 | 467 | 2† | 2† | 2† | 2† | 2† | 2† | 2† | 2† |
| 10 | 473 | 2† | 2† | 2† | 2† | 2† | 2† | 3† | 3† |
| 11 | 473 | 1† | 1† | 2† | 2† | 2† | 2† | 2† | 2† |
| 12 | 502 | 1† | 1† | 2† | 2† | 2† | 2† | 2† | 2† |
| R-Fenoldopam Mesylate | | | | | | | | | |
| 13 | 500 | 1† | 1† | 2† | 2† | 2† | 2† | 2† | 2† |
| 14 | 515 | 1† | 1† | 2† | 2† | 2† | 2† | 2† | 2† |
| 15 | 483 | 2† | 2† | 2† | 2† | 2† | 2† | 2† | 2† |
| 16 | 493 | 1† | 1† | 2† | 2† | 2† | 2† | 2†‡ | 2†‡ |

*Test material in 50% propylene glycol/50% sterile water mixture.
†Whitish in color
‡Subcutaneous hemorrhage The results from the intradermal injection study show that the drugs when injected intradermally result in some redness at the injection site.

Based on the results from this initial phase of dermal sensitization studies, a definitive challenge dermal sensitivity study was conducted, as described in Example 3. Briefly, thirty animals were divided into three test groups of 10 animals each. The animals in Group 5 were treated with fenoldopam mesylate, the animals in Group 6 with R-fenoldopam mesylate and the animals in Group 7 were treated with vehicles alone as a control.

All animals were initially treated with intradermal injections of the test compound, e.g., fenoldopam mesylate (Group 5) or R-fenoldopam (Group 6), in a 1:1 mixture of propylene glycol:water or in a mixture of Freund's Complete Adjuvent (FCA) in propylene glycol:water. The drug concentration in these vehicle mixtures was 40 mg/mL (see Table 4 in Example 3). The animals were also treated with FCA in water alone. The animals in Group 7 received the same three formulations, except for the absence of fenoldopam.

One week after the intradermal injections, each of the test formulations was applied topically to the injection site. The topical application, in the form of a saturated patch of filter paper, was left in place for 48 hours.

Two weeks after the topical application, the animals in groups 5 and 6 received a challenge dose of 40 mg/mL of the test compound in PG:water, applied topically to a naive site. On the opposing side of the animal, the vehicle alone (PG:water) was applied. The animals in Group 7 received the vehicle alone on both sides. 24 hours after the topical challenge dose, the site was scored for dermal sensitization using the four-point scale given above. The dermal reaction scores to the challenge application for each animal are shown in Tables 4A–4B.

TABLE 4A

Individual Dermal Reactions to Challenge Application-
Definitive Study

| | Test Material Hour | | Control Material Hour | |
|---|---|---|---|---|
| Animal Number | 24 | 48 | 24 | 48 |
| Group 5-Test (Fenoldopam Mesylate) | | | | |
| 17 | 1 | 1 | 0 | 0 |
| 18 | 1 | 1 | 0 | 0 |
| 19 | 1 | 1 | 0 | 0 |
| 20 | 1 | 1 | 0 | 0 |
| 21 | 1 | 1 | 0 | 0 |
| 22 | 1 | 1 | 0 | 0 |
| 23 | 0 | 0 | 0 | 0 |
| 24 | 0 | 0 | 0 | 0 |
| 25 | 0 | 0 | 0 | 0 |
| 26 | 0 | 0 | 0 | 0 |
| Group 6-Test (R-Fenoldopam Mesylate) | | | | |
| 27 | 1 | 1 | 0 | 0 |
| 28 | 1 | 1 | 0 | 0 |
| 29 | 1 | 1 | 0 | 0 |
| 30 | 0 | 0 | 0 | 0 |
| 31 | 0 | 0 | 0 | 0 |
| 32 | 0 | 0 | 0 | 0 |
| 33 | 0 | 0$^d$ | 0 | 0 |
| 34 | 0 | 0 | 0 | 0 |
| 35 | 1 | 1 | 0 | 0 |
| 36 | 1 | 1 | 0 | 0 |

Test Material
The respective test material was applied as a 40 mg/mL concentration of test material in a 50% propylene glycol/50% sterile water mixture.
Control Material
50% propylene glycol/50% sterile water mixture.
$^d$Desquamation.

TABLE 4B

Individual Dermal Reactions to Challenge Application-
Definitive Study

| | Test Material | | | | | |
|---|---|---|---|---|---|---|
| Animal | Fenoldopam Mesylate | | R-Fenoldopam Mesylate | | Control Material | |
| Number | 24 | 48 | 24 | 48 | 24 | 48 |
| Group 7-Control | | | | | | |
| 37 | 0 | 0 | 0 | 0 | 0 | 0 |
| 38 | 0 | 0 | 0 | 0 | 0 | 0 |
| 39 | 0 | 0 | 0 | 0 | 0 | 0 |
| 40 | 0 | 0 | 0 | 0 | 0 | 0 |
| 41 | 0 | 0 | 0 | 0 | 0 | 0 |
| 42 | 0 | 0 | 0 | 0 | 0 | 0 |
| 43 | 0 | 0 | 0 | 0 | 0 | 0 |
| 44 | 0 | 0 | 0 | 0 | 0 | 0 |
| 45 | 0 | 0 | 0 | 0 | 0 | 0 |
| 46 | 0 | 0 | 0 | 0 | 0 | 0 |

Test Material
The respective test material was applied as a 40 mg/mL concentration of test material in a 50% propylene glycol/50% sterile water mixture.
Control Material
50% propylene glycol/50% sterile water mixture.

The data shows that fenoldopam mesylate and R-fenoldopam mesylate result in moderate dermal sensitization, with 6 of the 10 animals in Group 6 and 5 of the 10 animals in Group 6 scored as having "scattered mild redness"

Transdermal Dosage Forms

Transdermal delivery devices, also referred to herein as transdermal patches, suitable for use for delivery of fenoldopam are shown in FIGS. 2–5. In the patches described below, the drug reservoir or matrix includes fenoldopam, which as defined above, is intended to include the racemate, the active R-enantiomer or a mixture of the R- and S-enantiomers in a ratio sufficient to enhance skin penetration of at least the R-enantiomer.

Figure 4:
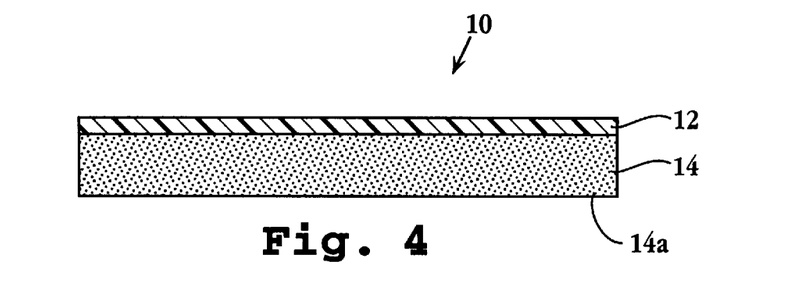
FIG. 4 shows an adhesive matrix transdermal patch having an impermeable backing and a fenoldopam-containing adhesive polymer matrix.

FIG. 4 illustrates one of the more simple types of transdermal devices, a fenoldopam adhesive matrix transdermal patch 10, and a basic embodiment of the present invention. Patch 10 includes an impermeable backing layer 12 and an adhesive matrix 14 which serves both as a reservoir for fenoldopam and as a means of attaching the device to the skin of a patient. The matrix surface 14a is also referred to herein as a drug-permeable contact surface. This surface is in communication with the drug reservoir and is adapted to be placed against the patient's skin. While not shown in the figure, the patch will further include a removable impermeable layer, also referred to in the art as a release liner or removable peel strip, covering the contact surface during storage and prior to use to prevent drug release from the adhesive matrix.

Backing layer 12 functions as an occlusive layer that prevents loss of fenoldopam and any enhancers present in the adhesive matrix to the environment. Materials suitable for use as the backing layer are known to those of skill in the art, with one selection criteria being that the backing material be impermeable to fenoldopam and any enhancers. It is also preferable for manufacturing purposes that the backing layer be mechanically strong enough to form a support onto which the fenoldopam-enhancer loaded adhesive can be cast. Exemplary backing material are polyester or aluminized polyester, such as the Scotchpak® medical films available from 3M Corporation (St. Paul, Minn.).

The adhesive matrix layer 14 in this embodiment serves both as a reservoir for fenoldopam and as contact surface for placement against a patient's skin. The fenoldopam is dispersed in the adhesive matrix. As used herein, the term "dispersed" refers to the distribution of fenoldopam throughout the matrix. The drug may be dispersed in a dissolved and/or undissolved state, but is preferably dissolved.

The adhesive matrix may be prepared by mixing together a solution of the adhesive polymer, which can be purchased commercially or prepared by dissolving the adhesive solid in a suitable solvent, with a solution of fenoldopam dissolved or evenly dispersed in selected enhancers. The mixture is poured into a mold or cast alone or on the desired backing material. The casting is then left for the solvent to evaporate at room temperature or in an oven at a slightly elevated temperature. After solvent evaporation, the adhesive matrix takes the form of an adhesive polymer film typically having a thickness in the range of about 50 to 100 $\mu$m.

The amount of fenoldopam loaded into the adhesive matrix can be varied by varying the concentration of fenoldopam in the casting mixture and the thickness of the adhesive matrix. The amount of fenoldopam in the adhesive matrix of a given patch area should be sufficient to provide for at least 6 hours of treatment, more preferably 48 hours of treatment and most preferably for a 2–3 day treatment period.

In a preferred embodiment of the invention, the transdermal device includes an enhancer effective to increase the skin permeation rate of fenoldopam to the skin. One preferred group of enhancers for use in transdermal administration of fenoldopam are fatty acids, fatty acid esters and fatty alcohols. Such compounds generally are hydrophobic or have limited water solubility and compounds with a molecular weight of between 150–300 daltons are preferable. Exemplary fatty alcohols include stearyl alcohol and oleyl alcohol. Exemplary fatty acids include oleic acid, lauric acid, myristic acid, palmitic acid, stearic acid, linoleic acid, and palmitoleic acid. Fatty acid esters containing more than 10 to 12 carbons can also be used, and examples include isopropyl myristate and the methyl and ethyl esters of oleic and lauric acid. Other compounds can also be used such as diethyl hexyl phthalate, octyldodecyl myristate, isostearyl isostearate, caprylic/capric triglyceride, glyceryl oleate, and various oils, such as wintergreen or eucalyptol.

Another group of preferred enhancers include low molecular weight alcohols, that is, alcohols having a molecular weight of less than about 200 daltons, more preferably less than about 150 daltons, most preferable less than 100 daltons, and which are relatively hydrophilic, generally having greater than 2 wt %, more preferably 5 wt %, most preferably 10 wt % solubility in water at room temperature. Exemplary alcohols include methanol, ethanol, propanol, butanol, benzyl alcohol, glycerin, and propylene glycol.

Other examples of enhancers suitable for use in the present invention are given in the review by Santus, G. C., et al., *Journal of Controlled Release*, 25:1–20 (1993), which is expressly incorporated by reference herein.

In another embodiment, the fenoldopam itself serves as a sort of enhancer, by causing vasodilation in the region of patch application. The vasodilation, e.g., enhanced blood flow, in the region results in increased uptake of the drug.

The adhesive used in an adhesive matrix type patch can be selected from a variety of adhesives available commercially and known to those in the art. For example, common adhesives are those based on poly isobutylene, acrylic, and silicone. The adhesive selected will depend in part on the enhancer or enhancers chosen and the amount of drug and enhancer loaded into the matrix. The adhesive must retain its adhesive properties in the presence of these additives, and provide tack for good instantaneous adhesion to the skin, good adhesion throughout the treatment period and clean removal from the skin after treatment. Some preferred adhesives include those available from Avery Chemical Corp and from National Starch and Chemical Company.

Figure 5:
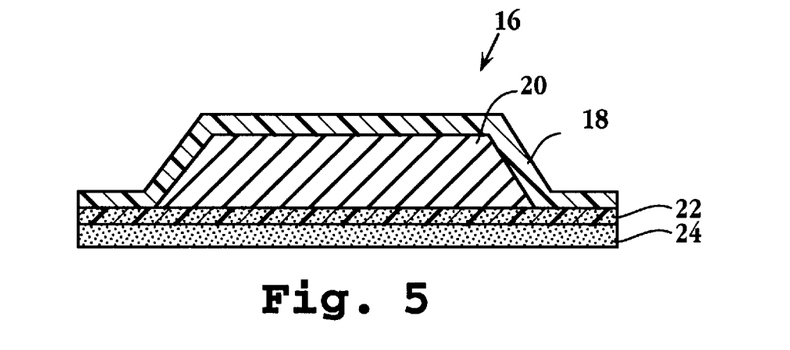
FIG. 5 shows a reservoir type transdermal patch having an impermeable backing, a drug depot, a porous membrane, and an adhesive layer, where the backing and the porous membrane are sealed at their peripheral edges, thus defining the drug depot.

Another example of a transdermal device is shown in FIG. 5, where a reservoir type transdermal patch 16 is illustrated. The patch includes an impermeable backing layer 18, a reservoir containing fenoldopam 20, a porous membrane 22, and an adhesive layer 24. Backing layer 18 may be the same as that described for the adhesive matrix type patch above.

Reservoir 20 is defined by the cavity formed when the backing layer is sealed to membrane 22 about the peripheral edge of the patch. The reservoir can take various forms, such as a simple solution of fenoldopam in a selected enhancer or enhancers, a gel of the drug and enhancer(s), where the solution or gel can be contained directly in the reservoir or contained in the pores of a pad inserted within the reservoir.

Membrane 22 in its most simple function provides mechanical support for adhesive layer 24, which is prepared from an adhesive material selected as described above with respect to FIG. 2. The membrane and adhesive layers ideally are freely permeable to fenoldopam and the enhancers and materials with the requisite permeability can be selected readily by in vitro dissolution testing where patches with different membranes are placed in a large reservoir of water or buffer and the release of drug and/or enhancer is monitored as a function of time. Some preferred materials for use as membrane include microporous polyethylene (such as Celgard from Hoechst-Celanese available in a range of pore sizes and hydrophilicities) and non-woven materials, such as the non-woven polyesters available from Dexter Corp. (Windsor Locks, Conn.).

In a preferred embodiment of the invention, a transdermal device of the type shown in FIG. 5 is prepared to include a first enhancer in the reservoir and a second enhancer in the adhesive matrix. Preferably, the first enhancer is a hydrophilic enhancer in which fenoldopam is freely soluble. The second enhancer is one suitable for plasticizing the stratum corneum, such as a fatty alcohol, a fatty acid ester or a fatty acid.

Figure 6:
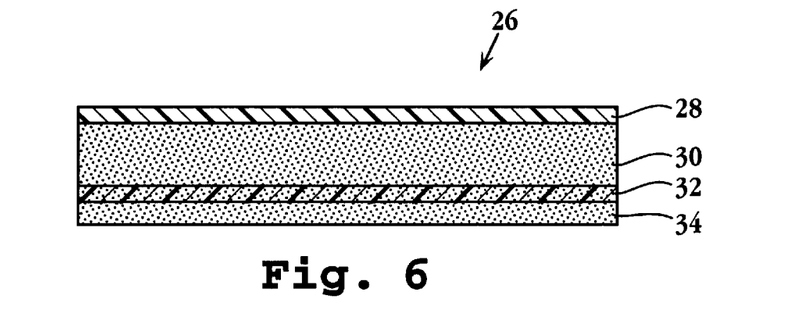
FIG. 6 shows a monolithic matrix transdermal patch having an impermeable backing, a drug depot comprising a polymer matrix in which drug is dispersed, an optional porous membrane, and an adhesive layer.

FIG. 6 illustrates another type of transdermal patch for use in administration of fenoldopam. Seen here is a monolithic matrix type transdermal patch 26, which includes an impermeable backing layer 28, a monolithic matrix layer 30, an optional porous membrane layer 32, and an adhesive layer 34. The backing, membrane, and adhesive layers are selected as described above for the embodiments of FIGS. 4 and 5. The porous membrane provides structural support for the adhesive layer which simplifies the manufacturing of the device. The monolithic matrix layer is distinguished from the adhesive matrix of FIG. 4 where the monolith serves both as the drug reservoir and the skin adhesive.

The monolithic matrix of FIG. 5 is prepared from a material suitable for holding in a solid form the fenoldopam-enhancer solution. For example, various polymers such as hydroxy ethyl methacrylate (HEMA) ethyl methacrylate (EMA) blends, polyvinyl alcohols, polyvinyl pyrrolidine, gelatin, pectin, and other hydrophilic polymers can hold large volumes of solvent. The monolithic matrix can also include microporous particles incorporated into a polymer or adhesive. The absorbent microparticles hold the drug and/or enhancers, and the use of microporous particles in transdermal patches is disclosed by Katz et al. in U.S. Pat. No. 5,028,535, Sparks et al. in U.S. Pat. No. 4,952,402, and Nuwayser et al. in U.S. Pat. No. 4,927,687, all of which are hereby expressly incorporated by reference.

In another embodiment, the matrix of the transdermal patch includes liposomes, where the fenoldopam is entrapped in the liposomes. It will be appreciated that liposomes containing fenoldopam can be present in the reservoir of any of patch designs shown in FIGS. 4–7. Formation of liposomes is readily done by one of skill in the art and has been described, for example, by Szoka, F., et al. (*Ann. Rev. Biophys. Bioeng.*, 9:467 (1980)) and in U.S. Pat. No. 4,235,871, which are hereby incorporated by reference.

Figure 7:
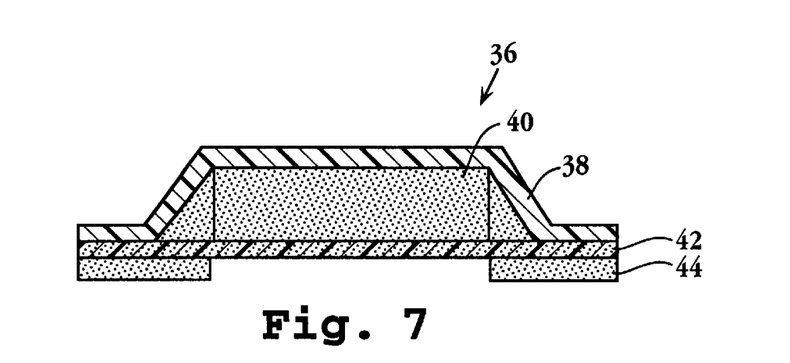
FIG. 7 shows a transdermal patch having an impermeable backing, a monolithic fenoldopam-containing matrix, a porous membrane, and a peripheral adhesive layer that is in contact with a non-active surface area.

FIG. 7 illustrates an embodiment of a transdermal patch 36, which includes a backing layer 38, a drug reservoir 40 and a membrane 42, as described above. In this patch, the adhesive layer 44 is about the periphery of the patch and serves to secure the patch to the skin of a patient. The membrane is directly in contact with the skin when applied to a patient, with the fenoldopam and enhancer passing directly from the reservoir through the membrane to the skin.

In one embodiment of the invention, the transdermal device includes R-fenoldopam in the drug matrix. Also included in the drug matrix is an amount of the pharmacologically inactive enantiomer S-fenoldopam effective to enhance the skin penetration rate of R-fenoldopam. In this case, S-fenoldopam is added in an amount sufficient to change a thermodynamic property of the disproportionate enantiomer mixture, such as a change in solubility or melting temperature, relative to the R-enantiomer. Preferably, sufficient S-fenoldopam is added to lower the melting point and/or to increase the solubility of R-fenoldopam in the skin, to achieve an increase in permeation of R-fenoldopam. Disproportionate mixture of enantiomers have been studied by others, such as Dwivedi, S. K., et al., *Intl. J. Pharm.*, 87:95–104 (1992) and Lawter, U.S. Pat. No. 5,114,946, and these references are expressly incorporated by reference herein.

In another embodiment, the transdermal patch of the invention is used in combination with an iontophoretic device for enhanced delivery of R-fenoldopam. Iontophoresis is an alternative strategy to the use of enhancers or enantiomeric mixtures to drive fenoldopam through the skin. In an iontophoresis drug delivery device, a battery is connected to two electrodes in the device and the electrodes are placed on the skin. The drug is placed in contact with one electrode (for example, a positive drug is placed in contact with the positive electrode) and when a current of low voltage is applied across the electrodes, the drug will migrate through the skin toward the opposite electrode, thereby entering systemic circulation. Typically, the amount of drug delivered is a function of the applied current and the treatment time, and these parameters are known to those of skill in the art. Iontophoresis and commercially available iontophoretic devices are discussed, for example, by Ranade, V.V. et al, *DRUG DELIVERY SYSTEMS*, CRC Press, Chapter 6, (1996); Tyle, P. *Pharmaceutical Res.*, 3:318 (1986); and Banga, A. K., et al., *J. Controlled Release*, 7:1–24 (1988), which are incorporated by reference herein.

More generally, administration of fenoldopam in a variety of dosage forms for topical delivery of the drug is contemplated. Topical, as used herein, refers to application of a fenoldopam dosage form to a body surface, including, but not limited to, mucosal regions, such as the mouth (buccal, sublingual), nasal passages and vagina, rectal delivery, and application of a cream, gel, or the like to the skin.

IV. Treatment Methods

The invention includes, in another aspect, a method of treating a subject for hypertension. As discussed above in the Background section, a common consequence of surgery in many patients is an acute elevation of blood pressure in the immediate postoperative period. The incidence of postoperative hypertension has been reported to vary from 4% in general surgical patients to as high as 70% in patients undergoing myocardial revascularization procedures. In these cases, postoperative hypertension may begin as soon as 10 minutes after completion of surgery and usually resolves itself within 4 hours. In those patients who experience postoperative hypertension for 3 hours or longer, there is an increased incidence of cardiac arrhythmia, congestive heart failure, increased bleeding, disruption of vascular suture lines, myocardial ischemia and cerebrovascular accident. It is, therefore, necessary to prevent postoperative hypertension.

Accordingly, the transdermal device of the present invention is effective in such situations to prevent postoperative hypertension. In patients where the probability of postoperative hypertension is high, the fenoldopam transdermal patch described above is affixed to the patient's skin at a time sufficiently prior to surgery to achieve a therapeutic blood concentration of the drug in the postoperative period.

In another aspect, the invention includes a method of treating a patient experiencing impaired renal function, either of a chronic or acute nature. Reduced or acute renal function is defined as rapid deterioration in renal function sufficient to result in accumulation of nitrogenous wastes in the body. Approximately 5of all hospitalized patents develop acute renal failure, and in some setting such as intensive care units, acute renal failure occurs in up to 20% of patients.

Urine formation begins with glomerular ultrafiltration of blood delivered to the kidneys, proceeds through tubular processing of the ultrafiltrate by secretion and absorption, and ends by excretion of urine through the ureters, bladder and urethra. Acute renal failure can be due to a dysfunction in any one or more of these steps, including decreased renal perfusion (prerenal azotemia), renal parenchymal disorders (renal azotemia) or obstruction to urine flow (postrenal azotemia).

Prerenal azotemia is the cause of 40–80% of acute renal failure cases, and is reversible if treated properly. A decrease in renal perfusion sufficient to lower glomerular capillary perfusion pressure can occur following extracellular fluid volume loss, such as in gastrointestinal hemorrhage, burns and diarrhea, or sequestration, such as pancreatitis, peritonitis and muscle crush injuries. Conditions such as severe congestive heart failure, sepsis and liver disease can also be accompanied by reduced renal perfusion.

Acute renal failure can also result as a side effect from other pharmacologic agents, such as nonsteroidal anti-inflammatory drugs which can cause a decrease in the synthesis of renal vasodilatory prostaglandins, leading to renal vasoconstriction and acute renal failure.

In these conditions and others, the patient suffering from or patients with a probability of developing acute renal failure can be treated with the fenoldopam-containing transdermal patch described above. Suitable dosages for acute renal failure can be determined by those of skill in the art.

Another clinical setting in which the patch of the invention is useful is in patients undergoing a surgical procedure and with a likelihood of experiencing increased blood pressure. Administration of fenoldopam can be used for blood pressure reduction to normal or subnormal levels to control bleeding and/or to reduce cardiovascular stress during surgery. In this embodiment, the transdermal patch is applied at a time before surgery sufficient to achieve a therapeutic blood concentration of fenoldopam during surgery.

Chronic renal failure is typically characterized by renal injury of a more sustained nature that is not reversible and which lead to progressive destruction of nephron mass. Common mitigating causes of chronic renal failure include glomerulonephritis, diabetes mellitus and hypertension. Patients suffering from chronic renal failure, in an embodiment of this aspect of the invention, are treated by administration of fenoldopam transdermally, as described above. For such a chronic condition, transdermal patches would preferably include sufficient drug to administer a therapeutically effective dose of a period of at least about 48 hours, more preferably for a period of 2–3 days.

V. Examples

The following examples describe the procedures for measuring the skin flux rate of fenoldopam in vitro and for the dermal sensitization studies. The examples are in no way intended to limit the scope of the invention.

Example 1

In vitro Skin Permeation Rate

Skin permeation rates of various fenoldopam mesylate and fenoldopam free base formulations were determined using static Franz diffusion cells having a receiving volume of 7 mL and an active area of 0.64 cm$^2$. The receiving compartment of the cells was filled with ammonium phosphate buffer, pH 4.0. The receiving compartment was stirred at 300 RPM and the temperature was maintained at 32° C. for the duration of the study.

Human cadaver skin was obtained from a skin bank in "pre-peeled" condition with the stratum corneum removed. The skin was stored in an ammonium phosphate solution until use. Skin punches were placed on the diffusion cells with the outer skin layers facing the donor compartment. Each of the test formulations described below was placed in the donor compartment (n=3 for each formulation) and the amount of drug permeated across the skin was determined as a function of time by sampling the receiver compartment and analyzing for drug content.

A. Test Formulations

Saturated solutions of fenoldopam mesylate in the following solvents were prepared: methanol/propylene glycol (90/10), dimethylsulfoxide (DMSO), lactic acid plus mesylate salt, and a 1:2 (vol/vol) mixture of DMSO and propylene glycol.

Saturated solutions of fenoldopam base (approximately 6base) in the following solvents were prepared: lactic acid, DMSO, DMSO/propylene glycol (1:2 vol/vol) and 2-pyrrolidone.

The results are shown in FIGS. 2A–2B and 3A–3B.

Example 2

Dermal Sensitization Studies

A. Animals

Guinea pigs (strain: CR1 (HA)BR) were obtained from Charles River Laboratories. The animals were young adults, weighing between 350–550 g at the start of the study. Each animals was housed individually and fed ad libitum a certified B. Test Materials A stock solution of 50% propylene glycol/50% sterile water mixture was prepared as the control material and for preparation of the test materials.

On each day of testing, a 40 mg/mL fenoldopam mesylate or R-fenoldopam mesylate in 50% propylene glycol/50% sterile water solution was prepared using the stock solution.

The 40 mg/mL drug solution was diluted with the stock solution to prepare solutions of 30 mg/mL, 20 mg/mL and 10 mg/mL of both the racemate and the enantiomer. All test materials were used within 8 hours of preparation and were stored at room temperature until administered.

C. Irritation Screen

Sixteen guinea pigs were divided into the following groups:

TABLE 1

Animals for Irritation Study

| Group No. | Administration | Drug | No. of Animals |
|---|---|---|---|
| 1 | topical | fenoldopam | 4 |
| 2 | topical | R-fenoldopam | 4 |
| 3 | intradermal | fenoldopam | 4 |
| 4 | intradermal | R-fenoldopam | 4 |

The back and sides of each animals were clipped free of hair with an electric clipper and the clipped area was divided into four test sites. The four animals in Group 1 each received the four different concentrations of fenoldopam solutions, and in Group 2, the four animals each received the four concentrations of the R-fenoldopam solutions.

For the topical application, the test materials were placed on 2 cm×2 cm pieced of filter paper to saturation and allowed to remain in place on the animal for 24 hours. The test sites were overwrapped with a strip of Blenderm™ tape and secured with Elasoplast® tape. After 24 hours, the patches were removed and any residual material removed from the application sites using water or an appropriate substance and paper towels. The sites were scored on the following four-point scale for dermal reactions at approximately 24 and 48 hours after patch removal:

0=no reaction
1=scattered mild redness
2=moderate and diffuse redness
3=intense redness and swelling For the intradermal injection, the four animals in Group 3 were treated with intradermal injection of fenoldopam mesylate and the four animals in Group 4 were treated with intradermal injections of R-fenoldopam mesylate. The test materials were administered at concentrations of 40 mg/mL, 30 mg/mL, 20 mg/mL and 10 mg/mL by injecting each at a volume of 0.1 mL into a separate site on the shaved back of the test animal. The areas of intradermal injections were evaluated for dermal irritation on the four-point scale given above at 24 and 48 hours after injection. The test sites were clipped with an electric clipper before the first reading.

The results are shown in Tables 2–3.

Example 3

Dermal Sensitization Challenge Study

Thirty guinea pigs were obtained and cared for as set forth in Example 2.

The animals were divided into three test groups of 10 animals for treatment as summarized in Table 5.

TABLE 5

Summary of Challenge Study

| Group No. | No. Animals | Test Compound | Drug Formulation at Each Treatment Site | | |
|---|---|---|---|---|---|
| | | | Anterior | Medial | Posterior |
| 5 | 10 | fenoldopam mesylate | FCA:water[1] | PG:water[2] | FCA:PG:water[3] |
| 6 | 10 | R-fenoldopam mesylate | FCA:water[1] | PG:water[2] | FCA:PG:water[3] |
| 7 | 10 | control: no drug | FCA:water[1] | PG:water[2] | FCA:PG:water[3] |

[1]Freund's Complete Adjuvent diluted 1:1 with sterile water and no test compound
[2]Propylene glycol and sterile water, 1:1, with test compound at 40 mg/mL
[3]test compound suspended in PG:water and diluted with FCA to give a 40 mg test compound/mL.

On Day 1 of the study, an area approximately 4 cm×6 cm was clipped with an electric clipper along the midline over the shoulder region of each animal in the test and control groups. Two rows of three 0.1 mL intradermal injections were made within the boundaries of a 2 cm×4 cm area, one row on each side of the midline. The injections in each row were as follows: at the anterior site, the animal received 0.1 mL of the prepared Freund's Complete Adjuvant (FCA) solution (Groups 5, 6 and 7); at the medial site, the animals received 0.1 mL of the respective prepared test material (Groups 5 and 6) or vehicle control (Group 7); and at the posterior site, the animals received 0.1 mL of the respective test material (drug in PG:water) further mixed with FCA solution (Groups 5 and 6) or a 1:1 dilution of the PG:water vehicle control in FCA.

On Day 7, the area of intradermal injection on each animal in Groups 5, 6 and 7 was clipped free of hair with an electric clipper. The clipped area was treated with 10% w/w sodium lauryl sulfate in petrolatum. An adequate amount of sodium lauryl sulfate to uniformly cover the injection sites was massaged into the skin.

On Day 8, the injection sites were wiped with a moist paper towel to remove any remaining sodium lauryl sulfate. The respective test material mixture (Groups 5 and 6) or the vehicle control alone (Group 7) was applied to a s cm×4 cm patch of filter paper to saturation. The patch was placed over the injection sites an covered with a strip of Blenderm™ tape. This was further secured with Elastoplast® tape would around the torso of the animal. This dressing was left in place for 48 hours, and the application site was unwrapped and any residual material was removed with water and a paper towel.

On Day 22, two weeks after the topical application, all the animals (Groups 5, 6 and 7) received a 40 mg/mL challenge dose of test material (Groups 5 and 6) or of the vehicles alone (Group 7). The hair was removed from an approximate 5 cm×5 cm area on the fight and left sides by clipping. The respective test material mixture was applied to a naive site on the right side of each animal in groups 5 and 6 on a 2 cm×2 cm piece of filter paper to saturation in the same manner as for the topical induction application. Each test material mixture was applied to one or two naive sites on the right side of each control animal in group 7 in the same manner. The left side of each animal in groups 5, 6 and 7 was treated with the vehicle control in the same manner. The patches were sealed to the fight and left sides for 24 hours under a strip of Blenderm™ tape overwrapped with Elasoplast®, to obtain complete occlusion. 24 hours later, the challenge sites were unwrapped and residual material was removed using water and paper towels. The challenge sites were scored with the 4-point scale given in Example 2 at this time and again at 48 hours.

The results are shown in Tables 4A–4B.

Although the invention has been described with respect to particular embodiments, it will be apparent to those skilled in the art that various changes and modifications can be made without departing from the invention.

What is claimed is:

1. A transdermal delivery device for administering racemic fenoldopam or R-fenoldopam to a subject, comprising
    (i) an impermeable backing layer;
    (ii) a matrix or reservoir adjacent the backing layer, and containing racemic fenoldopam or R-fenoldopam distributed therein in an amount sufficient for release over at least a 6-hour period at a skin permeation rate sufficient to achieve a therapeutic blood concentration; and
    (iii) a removable impermeable layer to prevent drug release from the matrix or reservoir prior to use.

2. The device of claim 1, wherein said matrix or reservoir further includes a penetration enhancer effective to enhance transdermal uptake of racemic fenoldopam or R-fenoldopam.

3. The device of claim 1, wherein said matrix or reservoir includes R-fenoldopam and an amount of S-fenoldopam, at a ratio of R:S fenoldopam enantiomers, which is effective to enhance the skin permeation rate of R-fenoldopam.

4. The device of claim 1, wherein said racemic fenoldopam or R-fenoldopam is entrapped in particles distributed throughout said reservoir or matrix, said particles being effective to release entrapped drug at a rate sufficient to achieve the desired skin permeation rate.

5. The device of claim 4, wherein the particles are composed of a hydrophilic polymer selected from the group consisting of polyvinyl alcohol, polyvinylpyrrilodone, polyacrylic acid and celluloses.

6. The device of claim 4, wherein said particles are liposomes.

7. The device of claim 1, which further includes a contact surface adjacent said reservoir or matrix, said contact surface selected from a drug-permeable membrane and an adhesive.

8. The device of claim 1, wherein said therapeutic blood concentration is effective to treat impaired renal function.

9. The device of claim 1, wherein said therapeutic blood concentration is effective to treat hypertension.

* * * * *